United States Patent [19]

Ono

[11] Patent Number: 5,015,763
[45] Date of Patent: May 14, 1991

[54] N-METHYL-α-DIALKYLAMIOACETOHY-DROXAMIC ACID COMPOUND

[75] Inventor: Mitsunori Ono, Kanagawa, Japan

[73] Assignee: Fuji Photo Film Co., Ltd., Kanagawa, Japan

[21] Appl. No.: 554,113

[22] Filed: Jul. 19, 1990

Related U.S. Application Data

[63] Continuation of Ser. No. 207,429, Jun. 16, 1988, abandoned.

[30] Foreign Application Priority Data

Jun. 17, 1987 [JP] Japan .................................. 62-150970

[51] Int. Cl.$^5$ .................... C07C 229/00; C07C 303/00
[52] U.S. Cl. .................................... 562/106; 562/564; 562/623
[58] Field of Search ........................ 562/106, 623, 564

[56] References Cited

FOREIGN PATENT DOCUMENTS 198453 of 1984 Japan .

OTHER PUBLICATIONS

J. Am. Chem. Soc., vol. 94, 1376 (1972).
Tetrahedron Letters, No. 8, 643–648 (1974).
Tetrahedron Letters, No. 41, 3613–3616 (1974).

*Primary Examiner*—Alan Siegel
*Attorney, Agent, or Firm*—Sughrue, Mion, Zinn, Macpeak & Seas

[57] ABSTRACT

An N-methyl-α-dialkylaminoacetohydroxamic acid represented by formula (I):

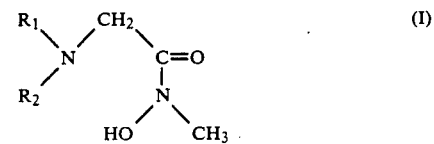

wherein $R_1$ and $R_2$, which may be the same or different, each represents a substituted or unsubstituted methyl group or a substituted or unsubstituted ethyl group.

3 Claims, No Drawings

N-METHYL-α-DIALKYLAMIOACETOHYDROXAMIC ACID COMPOUND

This is a continuation of application No. 07/207,429 filed June 16, 1988 now abandoned.

FILED OF THE INVENTION

This invention relates to an N-methyl-α-dialkylaminoacetohydroxamic acid compound which is useful as a deacylating agent.

BACKGROUND OF THE INVENTION

There has never been a published report on any species in the N-methyl-α-dialkylaminoacetohydroxamic acid genus except that N-methyl-α-diisobutylaminoacetohydroxamic acid is described in *J. Am. Chem. Soc.*, vol. 94, 1376 (1972) in Japanese patent application (OPI) No. 198453/84, and in *Tetrahedron Letters*, No. 8, 643–646 (1974). (The term "OPI" used herein means published unexamined Japanese patent application.) However, even these reports describe nothing about the properties or synthesis of this compound.

SUMMARY OF THE INVENTION

It is an object of the present invention to provide an N-methyl-α-dialkylaminoacetohydroxamic acid compound.

Other objects and effects of the present invention will be apparent from the following description.

The above objects of the present invention can be attained by a compound represented by formula (I):

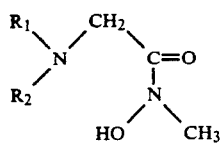

wherein $R_1$ and $R_2$, which may be the same or different, each represents a substituted or unsubstituted methyl group or a substituted or unsubstituted ethyl group.

DETAILED DESCRIPTION OF THE INVENTION

Preferred examples of the substituent of the group represented by $R_1$ or $R_2$ include a hydroxyl group, a carboxy group, a sulfo group, and a quaternary ammonium group. A carboxy group and a sulfo group are particularly preferred.

Examples of the compound of the present invention are as follows, although the scope of the present invention is not restricted thereby.

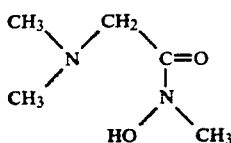

m.p.: 94–97° C.
pKa: 8.5 and 10.5
Highly soluble in, e.g., water, acetone, alcohols and THF

H-1:

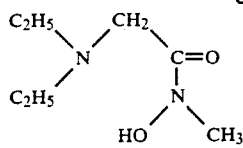

m.p.: 62–63° C.
pKa: 8.5 and 10.5
Highly soluble in, e.g., water, ethyl acetate, ether, THF and alcohols.

H-2:

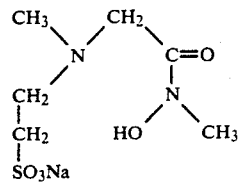

Amorphous and deliquescent powder
pKa: 7.5 and 10.2
Highly soluble in water and alcohols

H-3:

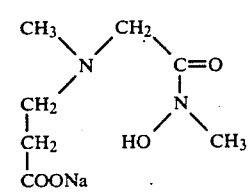

Amorphous powder
pKa: 5.2, 7.9 and 10.8.
Highly soluble in water and alcohols

H-4:

Each pKa value as shown is determined by the following method. Three solutions of a sample having concentrations of (1) $1 \times 10^{-2}$ M, (2) $1 \times 10^{-4}$ M, and (3) $1 \times 10^{-6}$ M are prepared by using a solvent mixture of water/ethanol (½ by weight) or water/tetrahydrofuran (½ by weight). Then the pKa values thereof are determined by using 0.2N HCl and NaOH with an automatic titrater (Model GT-05; made by Mitsubishi Chemical Industries, Ltd.). The pKa value of the sample at a concentration of 0 is calculated from the pKa values at the concentrations of (1) to (3) and referred to the apparent pKa value.

Processes for synthesizing the compound of the present invention may be roughly classified into the following (A) and (B) types.

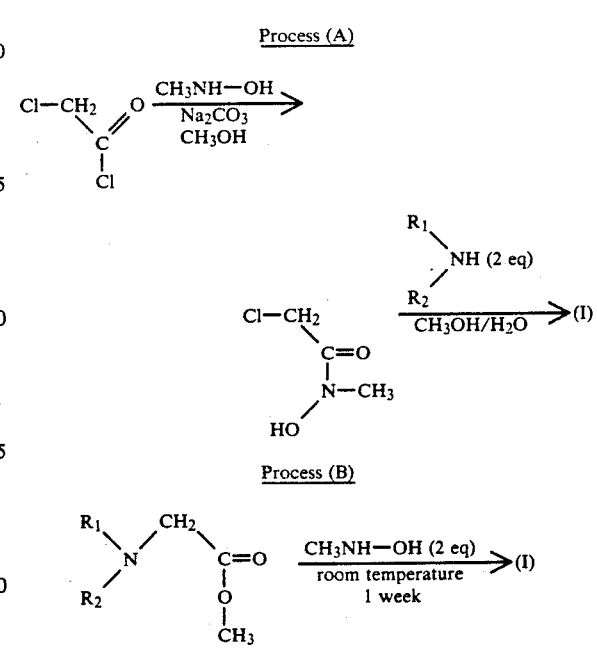

The compound of the present invention is useful the deacylation of an ester in an organic solvent under substantially neutral conditions. Deacylation is employed for eliminating a protective group during the synthesis of a pharmaceutical compound or for liberating a photographic reagent from a precursor thereof. It is known that an N-alkylhydroxamic acid compound exhibits a high nucleophilicity when dissociated in a solution of a pH value of 10 or above or in a specific reaction field such as a micelle system (pH 8 to 9). This fact is disclosed, for example, in Japanese patent application (OPI) No. 198453/84 and *Tetrahedron Letters*, No. 41, 3613–3616 (1974). (The term "OPI" used herein means published unexamined Japanese patent application.)

However, each deacylation process as described above should be effected at a high pH value or at a specific reaction field, which is unsuitable for common organic syntheses. In addition, an alkali metal salt employed for the dissociation of a hydroxamic acid is insoluble in organic solvents, which considerably restricts the application of the same as a nucleophilic agent in organic solvents.

These problems can be solved by using the compound of the present invention wherein an alkylamino group is introduced at an appropriate site in the molecule to thereby draw out a hydrogen atom therein. Thus, a substantially active derivative of a hydroxamic acid can be obtained. Further, the short-chain amino group makes the compound amphoteric, which is highly advantageous in organic syntheses.

The compound of the present invention differs from a conventional compound N-methyl-α-diisopropylacetohydroxamic acid in that the former shows a deacylating rate 50 to 100 times higher than that of the latter and that the former is amphoteric. The conventional α-diisopropyl compound is insoluble in aqueous solvents. Although the α-diisopropyl compound can be synthesized by the process (A) as shown above, the yield thus achieved is extremely low, i.e., 5% in total. Thus, the compound of the present invention is further superior to the conventional in view of the fact that it can be synthesized at an enhanced yield. Therefore the present invention is highly useful.

The following examples are given to illustrate the present invention in greater detail. The present invention should not be construed as being limited to these examples. Unless otherwise indicated, all parts, percents, ratios and the like are by weight.

EXAMPLE 1

Synthesis of H-1

21 g (0.48 mole) of NaOH was dissolved in a mixture of 100 ml off water and 50 ml of methanol. 40 g (0.48 mole) of N-methylhydroxylamine hydrochloride was added thereto and stirred under cooling. After 30 minutes, 28 g (0.24 mole) of N,N-dimethylglycine methyl ester was added thereto. The resulting mixture was stirred, sealed, and allowed to stand at room temperature for seven days. then, the solvent was distilled off under reduced pressure. To the white residue thus obtained, 200 ml of methanol was added and the mixture was thoroughly stirred. After filtering off insoluble matter, the filtrate was distilled under reduced pressure. To the obtained residue, 300 ml of acetone was added and the resulting mixture was heated and hot-filtered. The filtrate was distilled under reduced pressure and the oily material thus obtained was crystallized from acetone/ether and then recrystallized from acetone. Thus 27 g of Compound H-1 was obtained in the form of white crystals. m.p.: 94°–97° C.

EXAMPLE 2

Synthesis of H-2

Step 1:
To 180 ml of methanol, 25 g (0.3 mole) of N-methylhydroxylamine hydrochloride and 31.8 g (0.3 mole) of sodium carbonate were added and the resulting mixture at 5° to 10° C. Then the mixture was stirred at room temperature for 30 minutes. After filtering off insoluble matter, the filtrate was distilled under reduced pressure. To the pale yellow residue thus obtained, ethyl acetate was added. Then insoluble matters were filtered off and the filtrate was distilled under reduced pressure. The pale yellow oily material thus obtained was recrystallized from diethyl ether to thereby give 22.4 g of colorless N-methyl-α-chloroacetohydroxamic acid at a yield of 60.5%. m.p.: 42°–43° C.

Step 2:
2.47 g (0.02 mole) of the N-methyl-α-chloroacetohydroxamic acid as obtained above was dissolved in 20 ml of diethyl ether. To the solution thus obtained, 3.1 g (0.042 mole) of diethylamine was added and the resulting mixture was stirred at room temperature for five hours. Insoluble matters were filtered off and the filtrate was distilled under reduced pressure. The pale yellow oily material thus obtained was purified by silica gel column chromatography (eluent: $CHCl_3/MeOH$ (10/1 by weight)). Thus 3.0 g of pale yellow crystals were obtained. These crystals were recrystallized from hexane to thereby give 2.4 g of Compound H-2 in the form of colorless crystals at a yield of 75% m.p.: 62°–63° C.

EXAMPLE 3

Synthesis of H-3

13.8 g (0.086 mole) of sodium N-methyltaurinate was added to a mixture of 70 ml of methanol and 10 ml of water. After stirring the resulting mixture, 5.3 g (0.043 mole) òf N-methyl-α-chloro-acetohydroxamic acid was added thereto and the mixture was allowed to react at 50° C. for 30 minutes under a nitrogen stream. After cooling, the solvent was distilled off under reduced pressure. To the residue thus obtained, 50 ml of a mixture of methanol and acetone (1/1 by weight) was added. Insoluble matters were filtered off and the filtrate was distilled off under reduced pressure. The oily material thus obtained was purified by silica gel column chromatography (eluent: chlioroform/methanol (3/1 by weight) to thereby give 4.8 g of Compound H-3 in the form of an amorphous and deliquescent powder.

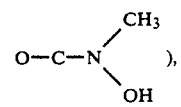

The field dissorption (FD) mass (electric dissociation) of the product was 249 ($M^+ + H$).

While the invention has been described in detail and with reference to specific examples thereof, it will be apparent to one skilled in the art that various changes and modifications can be made therein without departing from the spirit and scope thereof.

What is claimed is:
1. An N-methyl-α-dialkylaminoacetohydroxamic acid represented by formula (I):

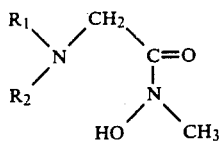

(I)

wherein $R_1$ and $R_2$, which may be the same or different, are selected from the group consisting of a methyl group and an ethyl group and may be optionally substituted with a substituent selected from the group consisting of a hydroxyl group, a carboxy group, a sulfo group, and a quaternary ammonium group.

2. An N-methyl-α-dialkylaminoacetohydroxamic acid as in claim 1, wherein a substituent of either $R_1$ or $R_2$ is selected from the group consisting of a hydroxyl group and a sulfo group.

3. An N-methyl-α-dialkylaminoacetohydroxamic acid selected from the group consisting of

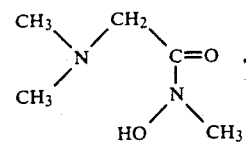

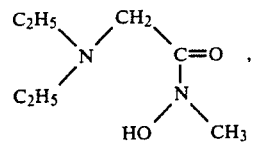

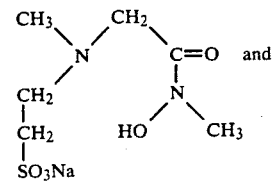

and

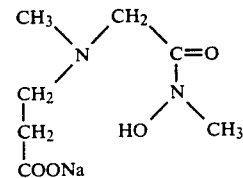

* * * * *